(12) United States Patent
Kesavan et al.

(10) Patent No.: US 9,533,319 B1
(45) Date of Patent: Jan. 3, 2017

(54) AEROSOL GENERATOR AND METHOD (71) Applicant: U.S. Army Edgewood Chemical and Biological Command, APG, MD (US)

(72) Inventors: Jana S Kesavan, Catonsville, MD (US); Jerold R. Bottiger, Aberdeen, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 290 days.

(21) Appl. No.: 14/288,721

(22) Filed: May 28, 2014

(51) Int. Cl.
*A62C 5/02* (2006.01)
*B05B 7/24* (2006.01)

(52) U.S. Cl.
CPC .................... *B05B 7/2491* (2013.01)

(58) Field of Classification Search
CPC .......... B05B 7/2491; B05B 7/24; B05B 7/241; B05B 7/2416; B05B 7/0012; A61M 11/005; A61M 15/0065; A61M 15/0085; B65D 83/75; B65D 83/752
USPC ............ 239/8, 337, 338, 34, 53, 55, 56, 418
See application file for complete search history.

(56) References Cited

U.S. PATENT DOCUMENTS

| | | | | | |
|---|---|---|---|---|---|
| 2,714,833 | A | * | 8/1955 | Gilbert, Jr. | G01N 21/72 239/424 |
| 4,125,225 | A | * | 11/1978 | Venghiattis | B05B 7/045 239/338 |
| 5,884,846 | A | * | 3/1999 | Tan | B05B 7/066 128/200.21 |
| 8,776,786 | B2 | * | 7/2014 | Kraft | A61M 11/06 128/200.22 |

* cited by examiner

*Primary Examiner* — Justin Jonaitis
(74) *Attorney, Agent, or Firm* — Ulysses John Biffoni (57) ABSTRACT

An aerosol generator includes a first body having a first end including an exit opening, and an oppositely positioned second end. An open channel second body is substantially positioned inside the first body and extends from the first end to the second end of the first body. An exit opening of the second body is positioned adjacent to the exit opening of the first end of the first body. An insert, which holds material to be aerosolized, is at least partially positioned inside the second body. An inlet opening receives compressed air into the first body. The compressed air flows towards the exit opening of the first end of the first body. The air flow creates a region of low pressure at the exit opening of the second body. The region of low pressure pulls the material out from the second body and aerosolizes the material. The aerosol generator is particularly effective in generating aerosols from small amounts of solid and liquid materials with minimal losses of material.

16 Claims, 6 Drawing Sheets

AEROSOL GENERATOR AND METHOD

GOVERNMENT INTEREST

The invention described herein may be manufactured, used, and/or licensed by or for the United States Government.

BACKGROUND

Technical Field

The embodiments herein generally relate to aerosol generators, and more particularly to aerosol generators used to aerosolize small amounts of powders and liquids with minimum losses.

Description of the Related Art

Many aerosol generators are available to aerosolize liquid and dry powder materials. Generally, all of these generators are designed for large quantities of materials and have significant losses in the generator. Sonic nozzles, collision nebulizers, and other medical nebulizers use a high air flow rate to aerosolize the material. These systems typically require gram quantities of material and have significant losses in the components that carry the powder or liquid through the generator. Accordingly, there remains a need for an aerosol generator that can aerosolize small amounts of powders and liquids with minimal losses.

SUMMARY

In view of the foregoing, an embodiment herein provides an aerosol generator comprising a first body comprising: a first end having an exit opening; and a second end positioned opposite to the first end. The aerosol generator further comprises an open channel second body substantially positioned inside the first body and extending from the first end of the first body to the second end of the first body, wherein an exit opening of the second body is positioned adjacent to the exit opening of the first end of the first body; an insert at least partially positioned inside the second body, wherein the insert is configured to hold material to be aerosolized; and an inlet opening that receives compressed air into the first body, wherein the compressed air flows towards the exit opening of the first end of the first body, wherein the air flow creates a region of low pressure at the exit opening of the second body, and wherein the region of low pressure pulls the material out from the second body and aerosolizes the material. Any of the first body and the second body may comprise a cylindrical tube.

The insert may comprise any of a tube and a flat sheet. The insert may comprise a groove. The material may comprise a mass of less than approximately 10 mg. The material may comprise any of a solid and a liquid. The exit opening of the second body may be smaller than the exit opening of the first end of the first body. Greater than approximately 97% of the material may be aerosolized. The compressed air may comprise a pressure of approximately 20 psi and may comprise an air flow rate of approximately 160 Lpm, and the air flow may occur for approximately one second. The inlet opening may be located proximate to the second end of the first body.

Another embodiment provides an aerosol generator comprising a first tube having an open first end and a closed second end; and a second tube substantially positioned inside the first tube and having a continuous open channel extending from a first end to a second end of the second tube, wherein an open first end of the second tube is substantially aligned with the open first end of the first tube, and wherein the second tube houses material to be aerosolized, wherein the first tube receives compressed air that flows towards the open first end of the first tube, wherein the air flow creates a region of low pressure at the open first end of the second tube, and wherein the region of low pressure pulls the material out from the second tube and aerosolizes the material. The aerosol generator may further comprise an insert at least partially positioned inside the second tube and comprising an end aligned with the open first end of the second tube, wherein the insert is configured to hold the material, wherein the insert comprises any of a tube or a flat sheet, and wherein the insert includes a groove. The material may comprise a mass of less than approximately 10 mg. The material may comprise any of a solid and a liquid. The open first end of the second tube may be smaller than the open first end of the first tube. Greater than approximately 97% of the material may be aerosolized. The compressed air may comprise a pressure of approximately 20 psi and may comprise an air flow rate of approximately 160 Lpm, and the air flow may occur for approximately one second.

Another embodiment provides a method of aerosolizing material, the method comprising receiving compressed air in a first body of an aerosol generator, wherein the aerosol generator comprises the first body and a second body positioned substantially within the first body, wherein the first body and the second body each comprise an exit opening adjacent to one another, wherein the exit opening of the first body is around the exit opening of the second body, and wherein the second body houses material to be aerosolized; configuring the first body to direct the compressed air towards the exit opening of the first body; creating a region of low pressure at the exit opening of the second body by a stream of compressed air being discharged from the exit opening of the first body; the region of low pressure pulling the material out from the second body into the stream of compressed air being discharged from the exit opening of the first body; and aerosolizing the material. The material may comprise any of a solid and a liquid comprising a mass of less than approximately 10 mg. The compressed air may comprise a pressure of approximately 20 psi and may comprise an air flow rate of approximately 160 Lpm.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide an aerosol generator used to aerosolize small amounts of powders and liquids, and in particular provides an aerosol generator used to aerosolize milligram quantities (e.g., <10 mg) of material (e.g., dry powder and liquid) with minimum losses, which is advantageous in testing with limited quantities of chemical-biological material that require a small amount of material aerosolized with minimum material losses. The cost of the materials may also limit the quantities available for aerosolization. Controlled chemical and biological agent materials are also available in limited quantities. Referring now to the drawings, and more particularly to FIGS. 1 through 8, where similar reference characters denote corresponding features consistently throughout the figures, there are shown preferred embodiments.

Figure 1:
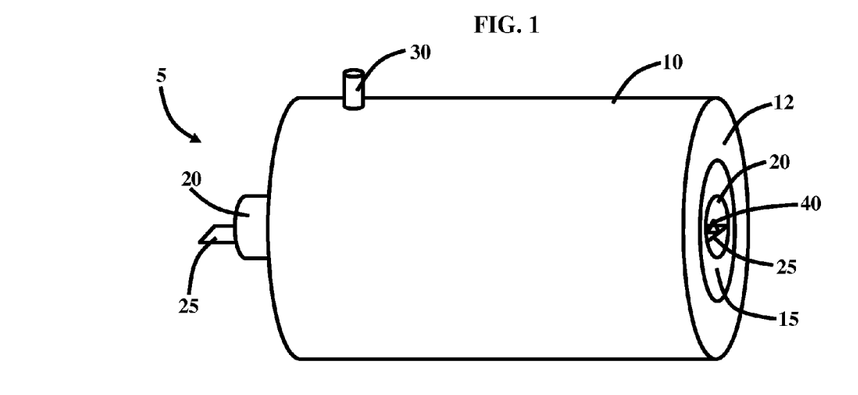
FIG. 1 illustrates a perspective view of an aerosol generator according to an embodiment herein.
Figure 2:
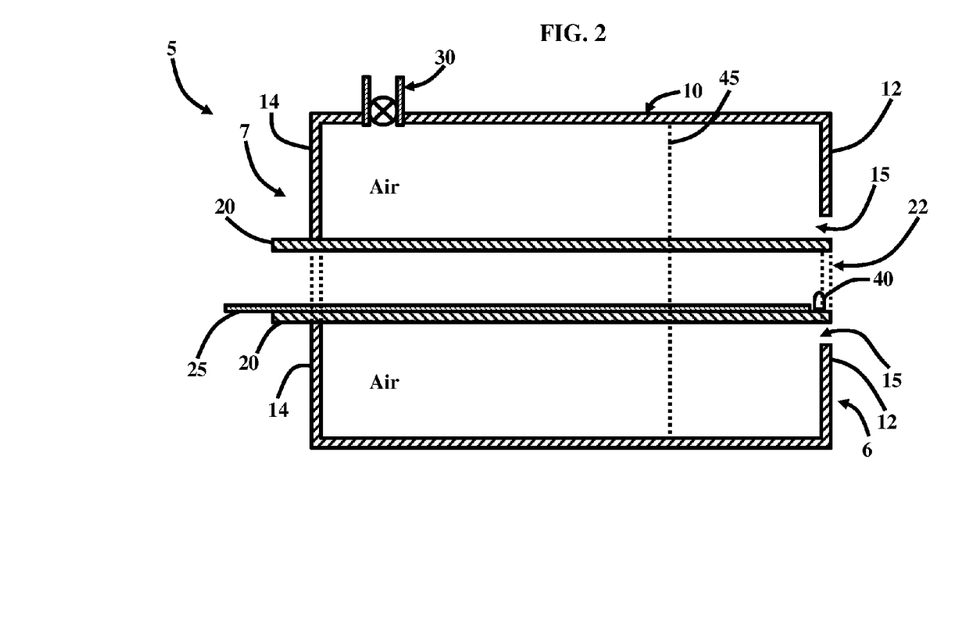
FIG. 2 illustrates a cross-sectional side view of the aerosol generator of FIG. 1 according to an embodiment herein.
Figure 3A:
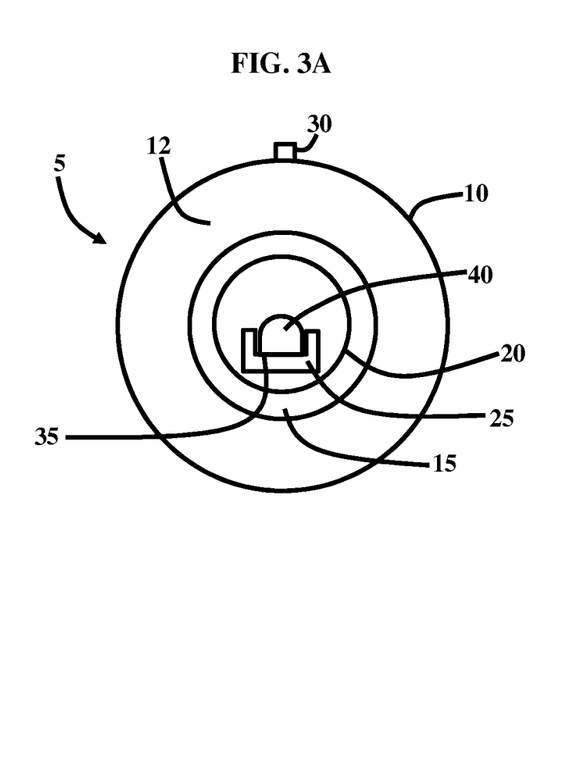
FIG. 3A illustrates a front view of the aerosol generator of FIG. 1 according to an embodiment herein.
Figure 3B:
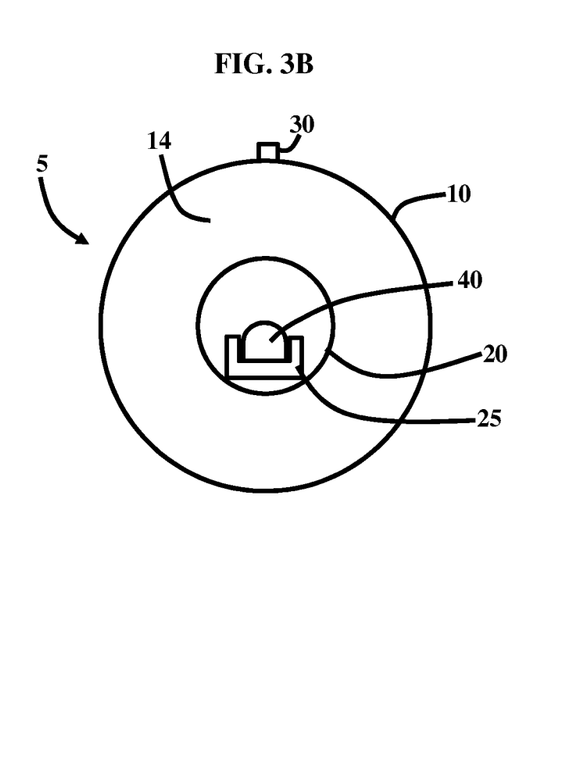
FIG. 3B illustrates a rear view of the aerosol generator of FIG. 1 according to an embodiment herein.

FIGS. 1 through 3B illustrate an aerosol generator 5 according to an embodiment herein. FIG. 1 illustrates a perspective view, FIG. 2 illustrates a cross-sectional side view, FIG. 3A illustrates a front view, and FIG. 3B illustrates a rear view of the aerosol generator 5. The aerosol generator 5 comprises a front portion 6 and a rear portion 7. The aerosol generator 5 further comprises a first body 10 comprising a first end 12 having an exit opening, and a second end 14 positioned opposite to the first end 12. An open channel second body 20 is substantially positioned inside the first body 10 and extends from the first end 12 of the first body 10 to the second end 14 of the first body 10, wherein an exit opening 22 of the second body 20 is positioned adjacent to the exit opening 15 of the first end 12 of the first body 10. An insert 25 is at least partially positioned inside the second body 20, wherein the insert 25 is configured to hold the material 40 to be aerosolized. The second body 20 and insert 25 may extend out from the second end 14 of the first body 10 in one example embodiment, and the insert 25 may extend even further out from the second body 20 at the rear portion 7 of the generator 5 in one example embodiment. The first body 10, second body 20, and insert 25 may be substantially planar to one another at a front portion 6 of the generator 5 in one example embodiment. A porous connector 45 may be positioned between the first body 10 and the second body 20 to provide support to retain the second body 20 in place.

The second body 20 is configured as an open channel body to permit the insert 25 to be inserted therein for placing the material 40 inside the second body 20. An inlet opening 30, which is located proximate to the second end 14 of the first body 10, receives compressed air into the first body 10, wherein the compressed air flows towards the exit opening 15 of the first end 12 of the first body 10, wherein the air flow creates a region of low pressure at the exit opening 22 of the second body 20, and wherein the region of low pressure pulls the material 40 out from the second body 20 and aerosolizes the material 40.

In one embodiment, any of the first body 10 and the second body 20 comprises a cylindrical tube. The material 40 may comprise any of a solid (e.g., powder) and a liquid (e.g., liquid droplets). The aerosol generator 5 can aerosolize any quantity of material 40. In one example embodiment, the amount of material 40 comprises a mass of less than approximately 10 mg. The exit opening 22 of the second body 20 is smaller than the exit opening 15 of the first end 12 of the first body 10. Moreover, the insert 25 may comprise any of a tube (e.g., a copper tube, etc.) or a flat sheet that slides into the second body 20. In one embodiment, the insert 25 includes a groove 35 that holds the material 40, which can assist in holding even smaller quantities of material 40. When the insert 25 is embodied as a flat sheet, the sheet may comprise any sturdy material including, for example, overhead transparency sheets which have very low weight to accurately measure a small amount of material 40 thereon. A sharp object (not shown) can be used to make an indent (e.g., groove 35) on the sheet 25 for the placement of the material 40.

Figure 4:
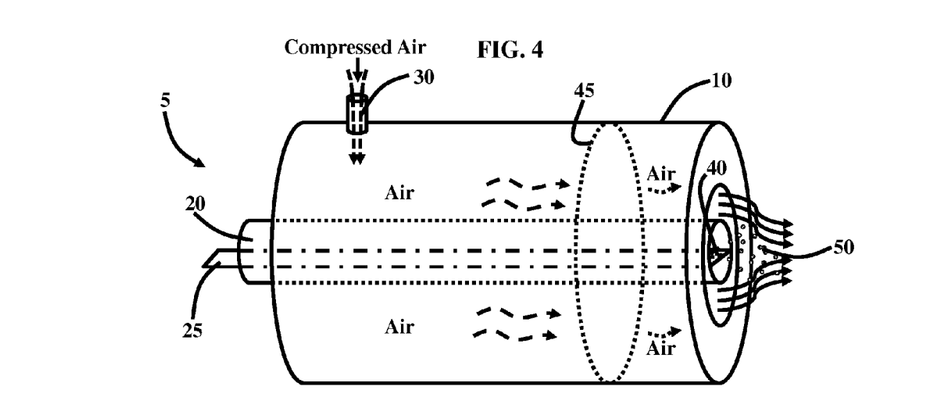
FIG. 4 illustrates a perspective view of the aerosol generator of FIG. 1 depicting a flow of air through the generator according to an embodiment herein.
Figure 5:
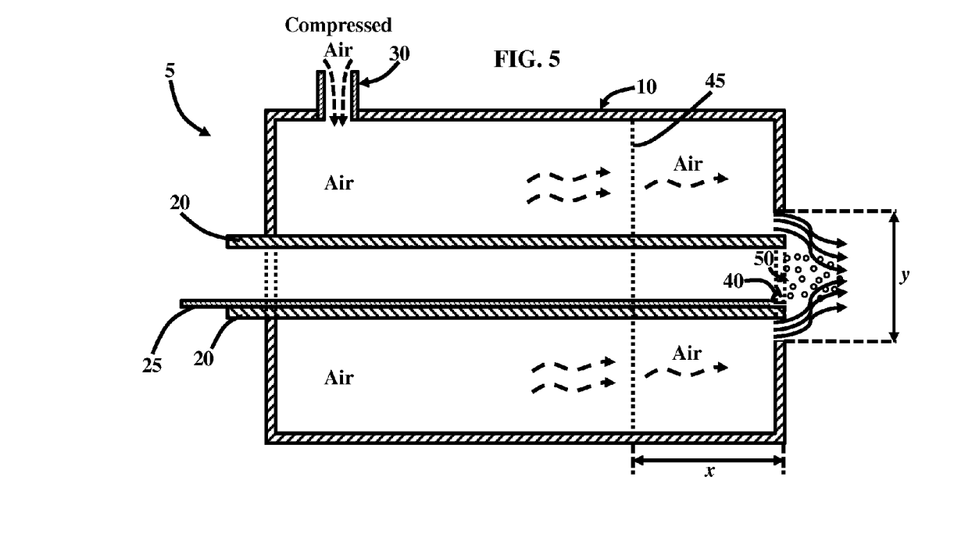
FIG. 5 illustrates a cross-sectional side view of the aerosol generator of FIG. 3 depicting a flow of air through the generator according to an embodiment herein.
Figure 6:
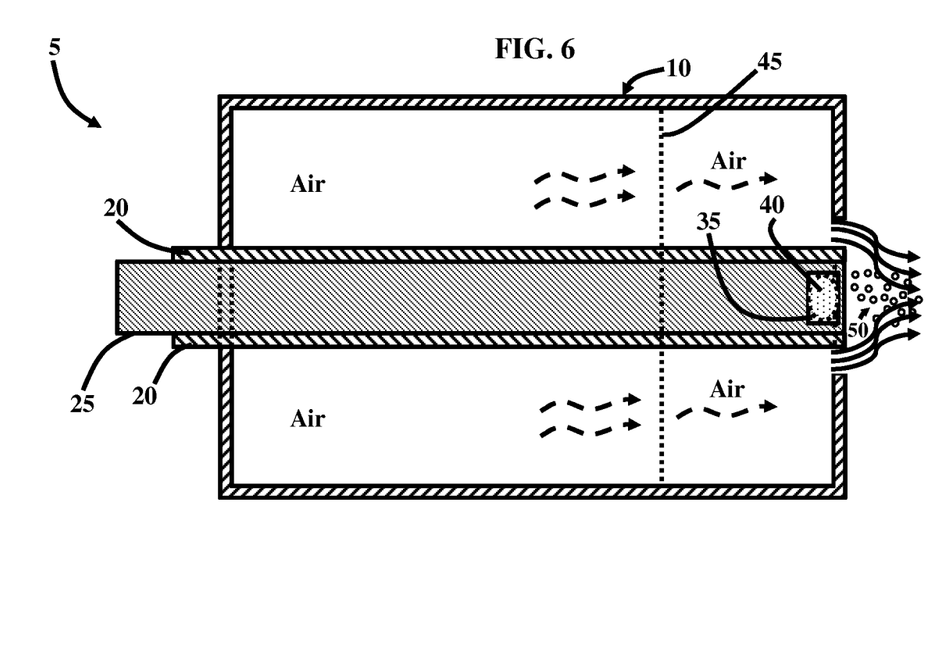
FIG. 6 illustrates a cross-sectional top view of the aerosol generator of FIG. 3 depicting a flow of air through the generator according to an embodiment herein.

FIGS. 4 through 6, with reference to FIGS. 1 through 3B, illustrate the aerosol generator 5 in operation according to an embodiment herein. FIG. 4 illustrates a perspective view, FIG. 5 illustrates a cross-sectional side view, and FIG. 6 illustrates a cross-sectional top view of the aerosol generator 5. Compressed air at a pressure of approximately 20 psi is delivered through the small inlet opening 30 using any appropriate and well known compressed air spraying mechanism (not shown). The air flows in the direction of the exit opening 15 of the first end 12 of the first body 10 because the second end 14 of the first body 10 is closed against the structure of the second body 20 to prevent air from exiting or attempting to exit from the second end 14 of the first body 10. The compressed air exits the exit opening 15 at high flow rate (e.g., approximately 160 Lpm). The low pressure created at the exit opening 22 causes the material 40 to be aerosolized to be pulled to the low pressure region and into the air stream 60 (shown in FIGS. 7B and 7C) due to the Bernoulli Effect where the material 40 breaks up into aerosol 50 by the shear forces of the air stream 60. The material 40 is separated as it is accelerated in the airstream 60 until it breaks into individual particles (e.g., aerosol) 50. The material 40 that is aerosolized is placed a few millimeters from the low pressure region (exit opening 22 of the second body 20) which reduces the material losses significantly.

In accordance with the embodiments herein, greater than 97% of the material 40 is aerosolized (e.g., aerosol 50). The losses (e.g., <3%) in the aerosol generator 5 are determined using fluorescent PSL microspheres, available from Powder Systems Limited. The fluorescent measurements indicate that approximately >97% of the material 40 is effectively aerosolized with <3% losses in the generator 5. The compressed air comprises a pressure of approximately 20 psi and comprises an air flow rate of approximately 160 Lpm, wherein the air flow occurs for approximately one second. Continual air flow is not needed and a one second air flow is adequate for the generation of the aerosol 50. Moreover, a manual delivery of a short (approximately one second) air flow is adequate to aerosolize the material 40 placed in the generator 5. This short burst of air can also be achieved by an automated system (not shown) that allows the air flow for a short time. Accordingly, the time for generation of the aerosol 50 is approximately one second as the air supply generally cannot be manually opened and closed in less than one second.

Figure 7A:
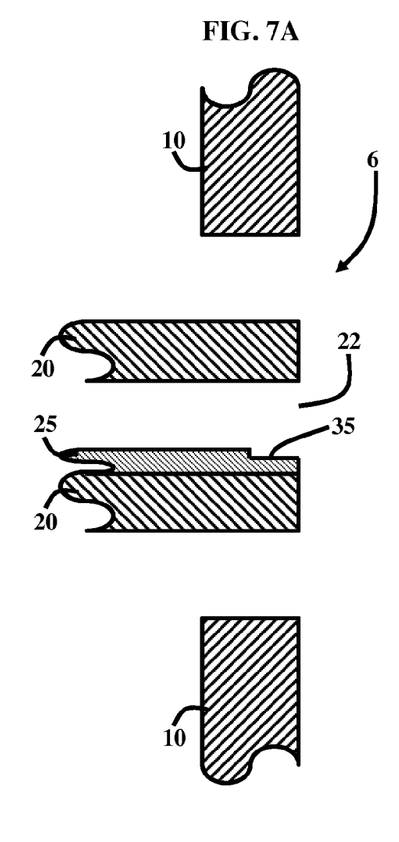
FIG. 7A illustrates a broken cross-sectional magnified side view of the front portion of the aerosol generator of FIG. 5 during a first stage of operation according to an embodiment herein.
Figure 7B:
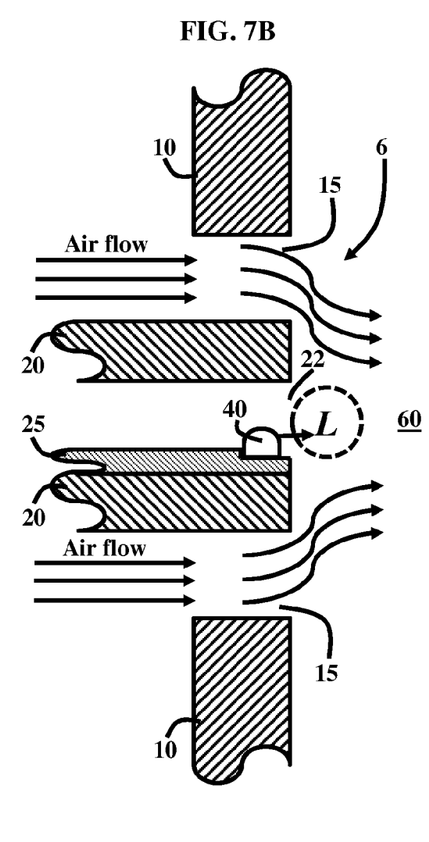
FIG. 7B illustrates a broken cross-sectional magnified side view of the front portion of the aerosol generator of FIG. 5 during a second stage of operation according to an embodiment herein.
Figure 7C:
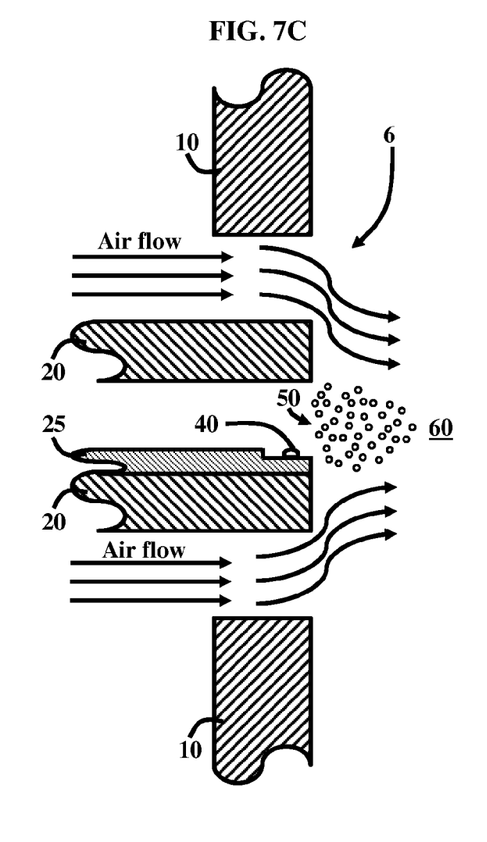
FIG. 7C illustrates a broken cross-sectional magnified side view of the front portion of the aerosol generator of FIG. 5 during a third stage of operation according to an embodiment herein.

FIGS. 7A through 7C, with reference to FIGS. 1 through 6, illustrate magnified views of three successive stages of operation of the aerosol generator 5. FIG. 7A illustrates a broken cross-sectional magnified side view of the front portion 6 of the aerosol generator 5 during a first stage of operation prior to filling the insert 25 with material 40 according to an embodiment herein. FIG. 7B illustrates a broken cross-sectional magnified side view of the front portion 6 of the aerosol generator 5 during a second stage of operation according to an embodiment herein. Here, the material 40 has been placed on the grooved insert 35 and compressed air has been introduced into the first body 10. The air flow continues to proceed out of the exit opening 15 of the first body 10 as air stream 60. The region of low pressure (shown as region L in FIG. 7B) pulls the material 40 out of the second body 20. FIG. 7C illustrates a broken cross-sectional magnified side view of the front portion 6 of the aerosol generator 5 during a third stage of operation according to an embodiment herein. In FIG. 7C, the material 40 aerosolizes into aerosol 50 as it enters the air stream 60 outside of the front of the aerosol generator 5 with less than 3% of material 40 remaining in the second body 20 of the generator 5.

In one example embodiment, the aerosol generator 5 may be configured using the following configurations and dimensions, which are merely provided as example configurations and dimensions, and the embodiments herein are not restricted to these particular configurations and dimensions. The first body 10 may be configured as a cylindrical tube with a length of approximately 1.7 inches and a diameter of approximately 1.5 inches. The exit opening 15 (shown as y in FIG. 5) may be configured with a diameter of approximately 0.2 inches. The second tube may be configured as a cylindrical tube with a length of approximately 2.9 inches and a diameter of approximately 0.15 inches. The inlet opening 30 for receiving the compressed air may be configured as a cylindrical tube with a length of approximately 1.0 inch and a diameter of approximately 0.5 inches. In FIG. 5, the length of x (the length from connector 45 to the front end 12 of the first body 10) is approximately 0.4 inches, in one example embodiment.

Figure 8:
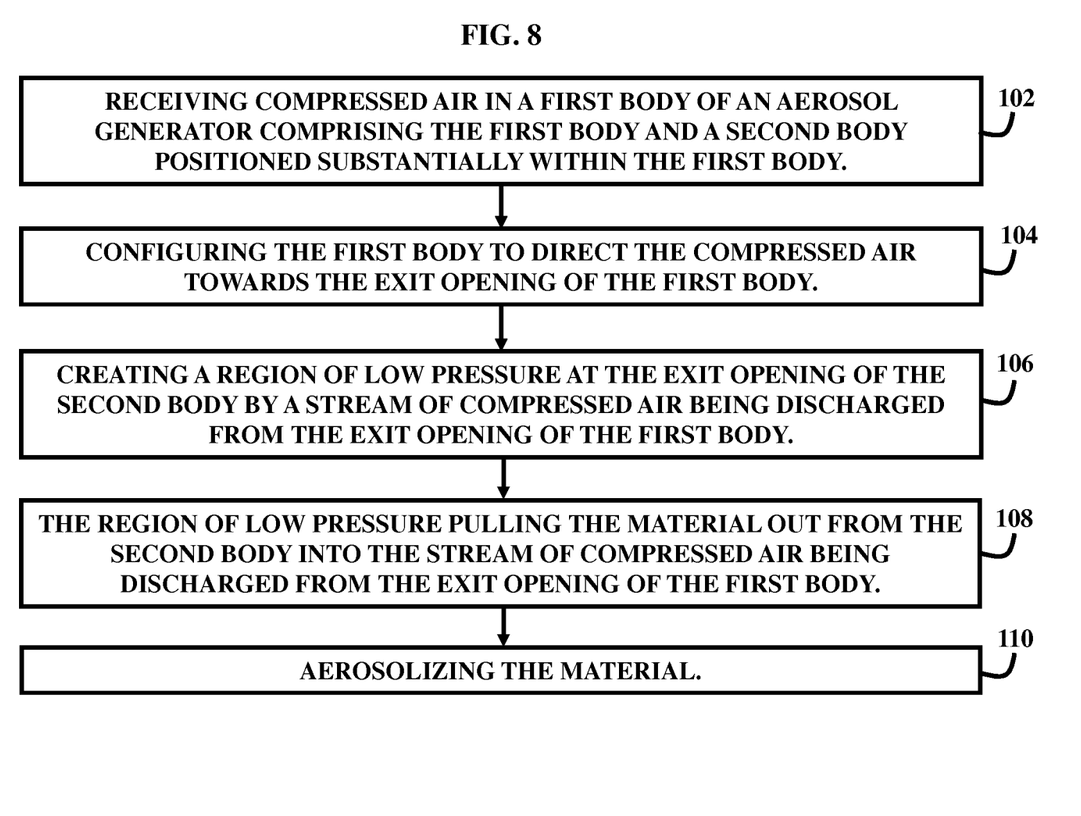
FIG. 8 is a flow diagram illustrating a preferred method according to an embodiment herein.

FIG. 8, with reference to FIGS. 1 through 7C, is a flow diagram illustrating a method of aerosolizing material 40 according to an embodiment herein. The method comprises receiving (102) compressed air in the first body 10 of the aerosol generator 5, wherein said aerosol generator comprises the first body 10 and the second body 20 positioned substantially within the first body 10, wherein the first body 10 and the second body 20 each include an exit opening 15 and 22, respectively, adjacent to one another such that the exit opening 15 of the first body 10 is around the exit opening 22 of the second body 20, and wherein the second body 20 houses the material 40 to be aerosolized; configuring (104) the first body 10 to direct the compressed air towards the exit opening 15 of the first body 10; creating (106) a region of low pressure L at the exit opening 22 of the second body 20 by a stream 60 of compressed air being discharged from the exit opening 15 of the first body 10; the region of low pressure L pulling (108) the material 40 out from the second body 20 into the stream 60 of compressed air being discharged from the exit opening 15 of the first body 10; and aerosolizing (110) the material 40, wherein the material 40 comprises any of a solid and a liquid comprising a mass of less than approximately 10 mg, and wherein the compressed air comprises a pressure of approximately 20 psi and comprises an air flow rate of approximately 160 Lpm.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. An aerosol generator comprising:
   a first body comprising:
      a first end having an exit opening; and
      a second end positioned opposite to said first end;
   an open channel second body substantially positioned inside said first body and extending from said first end of said first body to said second end of said first body, wherein an exit opening of said second body is positioned adjacent to said exit opening of said first end of said first body;
   an insert at least partially positioned inside said second body, wherein said insert is configured to hold a material to be aerosolized and to position a fixed amount of said material adjacent said exit opening of said second body; and
   an inlet opening that receives compressed air into said first body, wherein said compressed air flows towards said exit opening of said first end of said first body, wherein the air flow creates a region of low pressure at said exit opening of said second body, and wherein said region of low pressure pulls said material out from said second body and aerosolizes said material.

2. The aerosol generator of claim 1, wherein any of said first body and said second body comprises a cylindrical tube.

3. The aerosol generator of claim 1, wherein said insert comprises any of a tube or a flat sheet.

4. The aerosol generator of claim 1, wherein said insert includes a groove.

5. The aerosol generator of claim 1, wherein said material comprises a mass of less than approximately 10 mg.

6. The aerosol generator of claim 1, wherein said material comprises any of a solid and a liquid.

7. The aerosol generator of claim 1, wherein said exit opening of said second body is smaller than said exit opening of said first end of said first body.

8. The aerosol generator of claim 1, wherein greater than approximately 97% of said material is aerosolized by said aerosol generator.

9. The aerosol generator of claim 1, wherein said compressed air comprises a pressure of approximately 20 psi and comprises an air flow rate of approximately 160 Lpm, and wherein said air flow occurs for approximately one second.

10. The aerosol generator of claim 1, wherein said inlet opening is located proximate to said second end of said first body.

11. An aerosol generator comprising:
a first tube having an open first end and a closed second end;
a second tube substantially positioned inside said first tube and comprising a continuous open channel extending from a first end to a second end of said second tube, wherein an open first end of said second tube is substantially aligned with said open first end of said first tube, and
an insert at least partially positioned inside said second tube and having an end aligned with said open first end of said second tube, wherein said insert is adapted to hold a material to be aerosolized and to position a fixed amount of said material adjacent said open first end of said second tube, wherein said insert comprises any of a tube and a flat sheet, and wherein said insert includes a groove for holding said material; and
wherein said first tube receives compressed air that flows towards said open first end of said first tube, wherein the air flow creates a region of low pressure at said open first end of said second tube, and wherein said region of low pressure pulls said material out from said second tube and aerosolizes said material.

12. The aerosol generator of claim 11, wherein said material comprises a mass of less than approximately 10 mg.

13. The aerosol generator of claim 11, wherein said material comprises any of a solid and a liquid.

14. The aerosol generator of claim 11, wherein said open first end of said second tube is smaller than said open first end of said first tube.

15. The aerosol generator of claim 11, wherein greater than approximately 97% of said material is aerosolized by the aerosol generator.

16. The aerosol generator of claim 11, wherein said compressed air comprises a pressure of approximately 20 psi and comprises an air flow rate of approximately 160 Lpm, and wherein said air flow occurs for approximately one second.

* * * * *